(12) United States Patent
Porter

(10) Patent No.: US 9,439,750 B2
(45) Date of Patent: Sep. 13, 2016

(54) EMBOLECTOMY CAGE

(71) Applicants: Stryker Corporation, Kalamazoo, MI (US); Stryker NV Operations Limited, Dublin (IE)

(72) Inventor: Stephen C. Porter, Piedmont, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 156 days.

(21) Appl. No.: 13/707,375

(22) Filed: Dec. 6, 2012

(65) Prior Publication Data

US 2013/0158592 A1 Jun. 20, 2013

Related U.S. Application Data

(60) Provisional application No. 61/576,958, filed on Dec. 16, 2011.

(51) Int. Cl.
| | | |
|---|---|---|
| *A61M 29/00* | (2006.01) | |
| *A61F 2/01* | (2006.01) | |
| *A61B 17/221* | (2006.01) | |
| *A61B 17/22* | (2006.01) | |

(52) U.S. Cl.
CPC .............. *A61F 2/01* (2013.01); *A61B 17/221* (2013.01); *A61B 2017/22001* (2013.01); *A61B 2017/2212* (2013.01); *A61B 2017/22094* (2013.01)

(58) Field of Classification Search
CPC .............. A61F 2/82; A61F 2/86; A61F 2/90; A61F 2/915

USPC ................. 606/200, 159, 128, 127, 114, 113
See application file for complete search history.

(56) References Cited

U.S. PATENT DOCUMENTS

| | | | |
|---|---|---|---|
| 6,575,997 | B1 | 6/2003 | Palmer et al. |
| 8,052,640 | B2 | 11/2011 | Fiorella et al. |
| 2002/0058904 | A1 | 5/2002 | Boock et al. |
| 2004/0068288 | A1* | 4/2004 | Palmer et al. ................ 606/200 |
| 2004/0186551 | A1 | 9/2004 | Kao et al. |
| 2004/0199201 | A1 | 10/2004 | Kellett et al. |

(Continued)

FOREIGN PATENT DOCUMENTS

| | | |
|---|---|---|
| DE | 10 2010 045 367 | 11/2011 |
| WO | 2008034077 | 3/2008 |

OTHER PUBLICATIONS

PCT International Search Report and Written Opinion for International Application No. PCT/US2012/068281, Applicant Stryker Corporation, Forms PCT/ISA/210, 220, and 237, dated Feb. 19, 2013 (11 pages).

(Continued)

*Primary Examiner* — Katherine M Shi
*Assistant Examiner* — Mohamed Gabr
(74) *Attorney, Agent, or Firm* — Vista IP Law Group, LLP

(57) ABSTRACT

An embolectomy cage having an elongate axis and a circumference comprises a plurality of paired, closely spaced, substantially parallel, elongate members collectively defining a plurality of open cells, wherein individual elongate members of the pairs are connected at nodes located between respective pairs of axially adjacent cells and circumferentially adjacent cells, and wherein at least one elongate member spans each node without forming a connection to another elongate member.

12 Claims, 8 Drawing Sheets

(56) References Cited

U.S. PATENT DOCUMENTS

2009/0264979 A1\* 10/2009 Kao et al. .................... 623/1.11
2010/0318171 A1\* 12/2010 Porter et al. ................. 623/1.11
2012/0123466 A1    5/2012 Porter et al.

OTHER PUBLICATIONS

Office Action mailed Oct. 9, 2015 for European Application No. 12810462.7, (4 pages).

\* cited by examiner

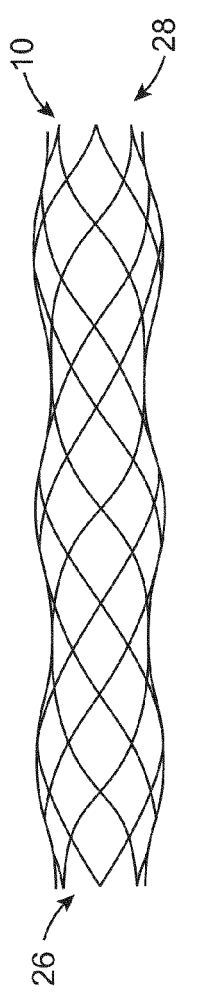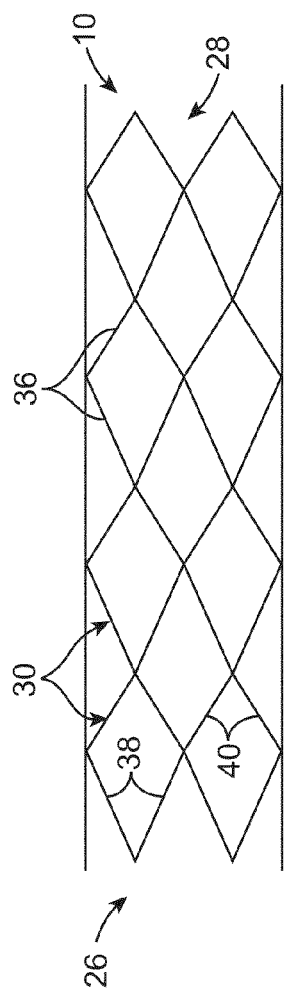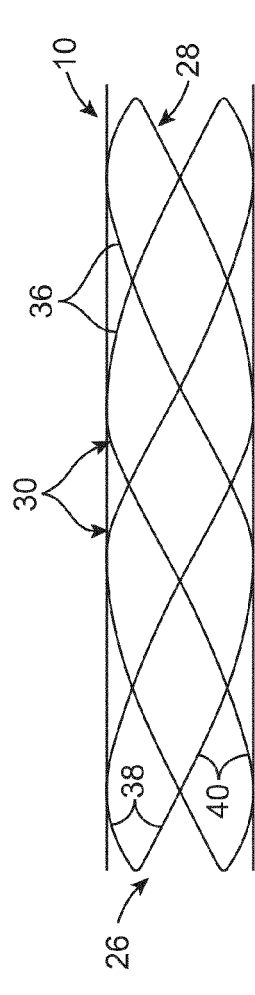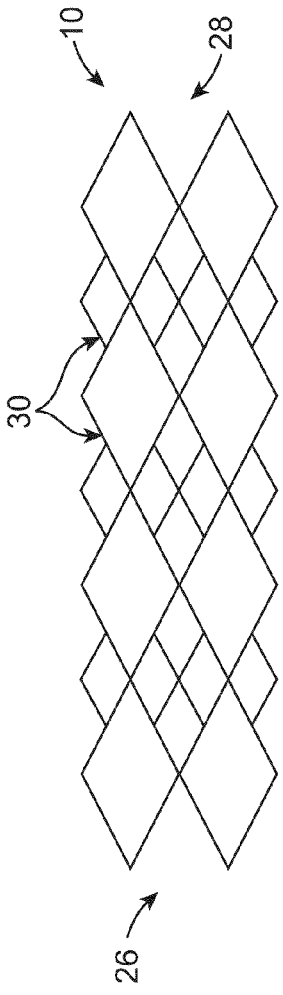

EMBOLECTOMY CAGE

RELATED APPLICATION DATA

The present application claims the benefit under 35 U.S.C. §119 to U.S. provisional patent application Ser. No. 61/576,958, filed Dec. 16, 2011. The foregoing application is hereby incorporated by reference into the present application in its entirety

FIELD

The present disclosure relates generally to medical devices. More particularly, the present disclosure relates to embolectomy cages with dual strut construction.

BACKGROUND

Blood thrombus, may embolize and form an embolus in a patient vasculature. Sometimes such emboli are harmlessly dissolved in the blood stream. At other times, however, such emboli may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot from the patient.

Embolectomy cages are used to treat strokes where blood flow in a vessel is blocked by an embolus. These devices function to remove the embolus and recanulate the vessel lumen by compressing the embolus into the lumen wall, macerating the embolus by pulling the device through the embolus, capturing the embolus by pulling the embolus into the interior of the device, breaking the embolus into smaller pieces to facilitate aspiration, anchoring the embolus so that it does not migrate distally during aspiration, and combinations thereof.

Prior art devices, such as those disclosed in U.S. Patent Publication Nos. 2002/0058904 and 2007/0208367, incorporated herein by reference in their entireties, create a radial force that tears through the embolus as the device expands, after which the embolus penetrates into the interior of the device to be captured in a dense net at the distal end of the device. In such devices, relatively high pressure needed to sever the fibrin networks of the blood clot forming the embolus. Other prior art devices tear the embolus from the wall of the vessel using a shear force, wherein an axial force is applied to the device in addition to radial forces to tear the embolus from the wall of the vessel.

Typical embolectomy cages have openings with areas in the range of about $5 \times 10^7$ µm² to about $3 \times 10^5$ µm². Struts forming the embolectomy cages are about 100 µm to about 40 µm wide. Smaller openings in embolectomy cages result in more struts, which, in turn, distribute the total radial force required to engage an embolus over a larger portion of the wall of the vessel. However, emboli do not engage well with smaller openings, due to an inability to penetrate the smaller openings.

Larger openings in embolectomy cages allow for better engagement of the embolus by the embolectomy cage, such as described in co-pending and co-owned U.S. Patent Publication No. 2012/0123466, incorporated herein by reference in its entirety. However, such larger openings reduce the number of struts, resulting in the total radial force required to engage the embolus being distributed over fewer struts. Because strut widths are typically within the above-listed range, this arrangement increases the local pressure that each strut places on the vessel wall, which could lead to vascular damage. Using wider struts to distribute the force over a greater area creates a device with greater bending stiffness.

SUMMARY

In one embodiment of the disclosed inventions, an embolectomy cage having an elongate axis and a circumference comprises a plurality of paired, closely spaced, substantially parallel, elongate members collectively defining a plurality of open cells, wherein individual elongate members of the pairs are connected at nodes located between respective pairs of axially adjacent cells and circumferentially adjacent cells, and wherein at least one elongate member spans each node without forming a connection to another elongate member. Optionally, two pairs of elongate members intersect at each node, with an elongate member of each pair spanning the respective node without forming a connection to another elongate member. One elongate member of each pair may be more flexible than the other. Alternatively or additionally, the elongate members of each pair have different cross-sectional geometries. In some embodiments, each cell comprises a first region bordered by one or more pairs of elongate members, and a second region bordered by one or more unpaired elongate members.

In other embodiments, each cell comprises a first region bordered by proximal pairs of elongate members, and a second region bordered by distal pairs of elongate members. The respective elongate members of the proximal and distal pairs maybe substantially the same length. Alternatively, the elongate members of the proximal pairs may have greater lengths than the elongate members of the distal pairs. In another alternative, the elongate members of the distal pairs may have greater lengths than the elongate members of the proximal pairs.

In some embodiments, each pair of elongate members forms a boundary between two adjacent cells. The cells may be ovoid or triangular in shape. The cells may also be substantially uniform in shape.

In still other embodiments, two elongate members connect at each node. Further, three elongate members may connect at each node. Moreover, four elongate members may connect at each node. Two elongate members may span each node without forming a connection to another elongate member.

In another embodiment, an embolectomy cage having an elongate axis, comprises a plurality of paired, closely spaced, substantially parallel, elongate members, each pair defining a slot between them, the pairs of elongate members collectively defining a plurality of cells, wherein individual elongate members of each of two pairs are connected at nodes between axially adjacent cells, and wherein the slots defined by the respective pairs span the node.

In yet another embodiment, an embolectomy cage having an elongate axis and a circumference, comprises a plurality of sets of closely spaced, substantially parallel, elongate members collectively defining a plurality of open cells, wherein each set comprises at least two elongate members, wherein individual elongate members of the sets are connected at nodes located between respective pairs of axially adjacent cells and circumferentially adjacent cells, and wherein at least one elongate member spans each node without forming a connection to another elongate member.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIG. 8A is a plan view of an embolectomy cage, according to yet another embodiment of the invention.

FIGS. 8B-8D are flat views of embolectomy cages, according to various embodiments of the invention.

DETAILED DESCRIPTION OF THE ILLUSTRATED EMBODIMENTS

Figure 1A:
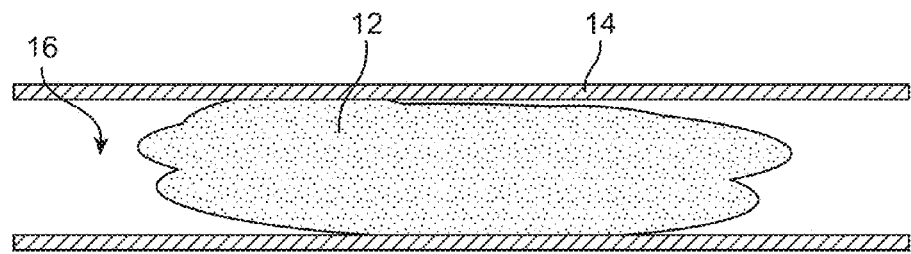
FIGS. 1A-1F are schematic views of an embolectomy cage, according to one embodiment of the invention, being used to remove an embolus from a vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIGS. 1A-1F illustrate various methods of removing an embolus 12 from a vessel 14 using an embolectomy cage 10. In FIG. 1A, an embolus 12 has occluded the lumen 16 of a vessel 14, cutting off blood flow through the vessel 14. The embolus 12 could be purely embolic, i.e., an embolus (such as a piece of thrombus) carried into serially smaller vessels until it lodged itself in a vessel 14 or at a bifurcation point (not shown). The embolus 12 could be purely thrombotic, i.e., a thrombus formed in a vessel wall until it occluded the vessel 14. Alternatively, the embolus 12 could be an embolically induced thrombotic clot, i.e., a thrombus formed adjacent an incompletely occluding embolus due to shear disturbance resulting from the embolus.

Figure 1B:
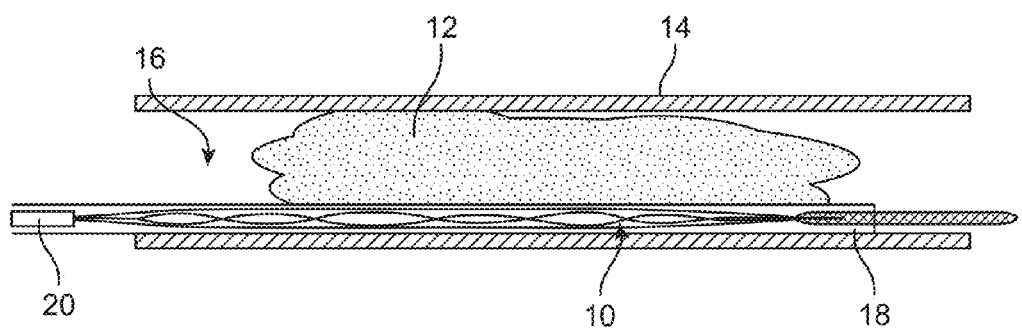

In FIG. 1B, a catheter 18 has been threaded past the embolus 12 along the wall of the vessel 14. Then an embolectomy cage 10 fixedly attached to a pusher wire 20 has been threaded through the catheter into the lumen 16 adjacent the embolus 12. Alternatively, the catheter 18 could have been threaded past the embolus 12 with the embolectomy cage 10 and the pusher wire 16 contained therein.

Figure 1C:
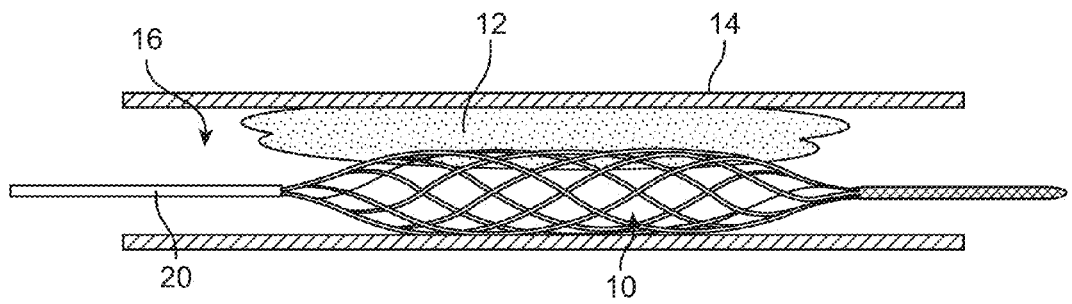

In FIG. 1C, the catheter 18 has been withdrawn proximally while maintaining the position of the embolectomy cage 10 relative to the embolus 12. The embolectomy cage 10 has expanded, either self-expanded or expanded by an external force, such as a balloon. The expanded embolectomy cage 10 exerts a radial force on the embolus 12, compressing it against the wall of the vessel 14. The embolectomy cage 10 has penetrated and at least temporarily secured itself to the embolus 12. Three non-mutually exclusive mechanisms can be used to dislodge the embolus 12 from the wall of the vessel 14.

Figure 1D:
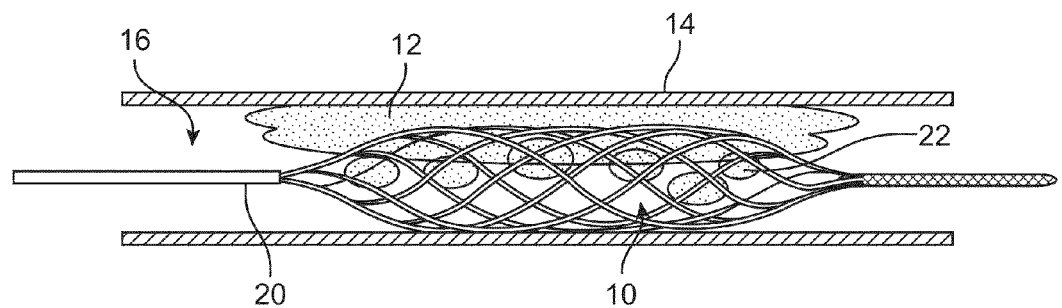

In FIG. 1D, the embolectomy cage 10 is repeatedly advanced distally and withdrawn proximally a small distance relative to the length of the embolus 12 and/or rotated around the longitudinal axis, to skive off small fragments 22 of the embolus 12 using a "cheese-grater-like" mechanism. The small fragments 22, which can be macerated by the "cheese-grater-like" mechanism, are subsequently removed by aspiration or filtration. The small fragments 22 also increase the surface area available to enzymes, which can, at least partially, dissolve the small fragments 22 of the embolus 12. After a first layer of the embolus 12 is skived off using this method, the embolectomy cage 10 can be further expanded and the skiving process repeated until the embolus 12 is removed from the vessel 14.

Figure 1E:
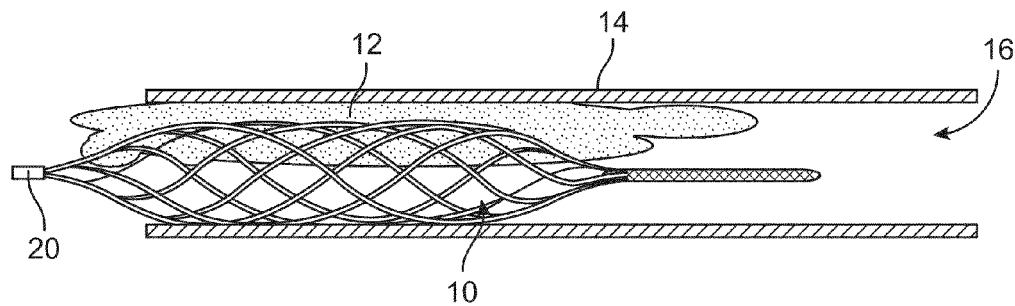

In FIG. 1E, the embolectomy cage 10 is withdrawn proximally by pulling on the pusher wire 20. As it moves proximally, the embolectomy cage 10 pulls the embolus 12 off of the wall of the vessel 14. The embolus 12 is subsequently removed with the embolectomy cage 10.

Figure 1F:
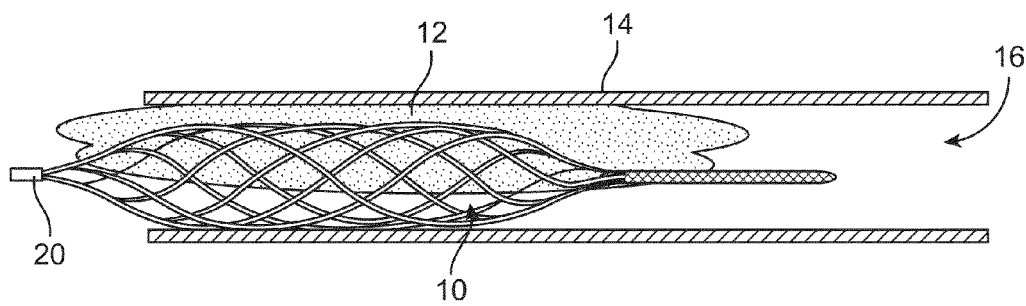

In FIG. 1F, when the embolectomy cage 10 expands adjacent the embolus 12, it penetrates into the embolus 12. This engagement of the embolectomy cage 10 with the embolus 12 temporarily secures the embolectomy cage 10 to the embolus 12. When force is applied along the longitudinal axis of the embolectomy cage 10, the engagement increases frictional forces between the embolectomy cage 10 and the embolus 12. As the embolectomy cage 10 is withdrawn proximally by pulling on the pusher wire 20, the embolectomy cage 10 pulls the embolus 12 off of the wall of the vessel 14. The embolus 12 is subsequently removed with the embolectomy cage 10.

As alluded to above, the steps depicted in FIGS. 1D and 1F can be used separately or in conjunction with one another to remove an embolus 12 from a vessel 14. A limiting factor in this removal method is the ability of the embolectomy cage 10 to engage with the embolus 12. The ability of an embolectomy cage 12 to engage an embolus 12 increases with the radial force the embolectomy cage 12 can exert on the embolus 12 without damaging the wall of the vessel 14 in which it is disposed. This factor, in turn, is affected by structure of the embolectomy cage 10.

Figure 2A:
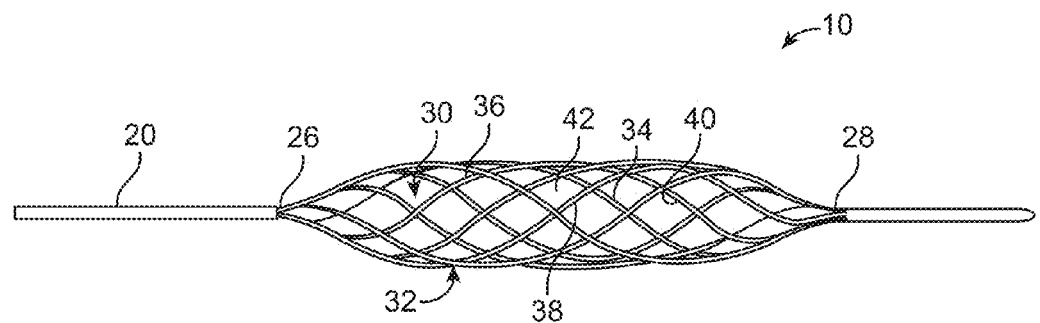
FIGS. 2A and 2B are perspective views of an embolectomy cage in respective closed and open conditions, according to another embodiment of the invention.
Figure 2B:
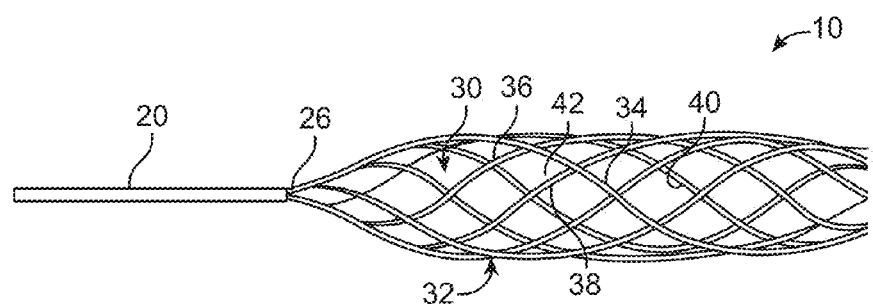

FIGS. 2A and 2B shows an embodiment of a device of the present invention in an expanded state, including cage 10 and pusher wire 20. In some embodiments, such as the one shown in FIG. 2A, the cage 10 is closed at both the proximal end 26 and the distal end 28 in the expanded state. In other embodiments, such as the one shown in FIG. 2B, the cage 10 is only closed at one end. In one embodiment (not shown), the cage 10 is open at both the proximal end 26 and the distal end 28. As shown in FIG. 2A, the proximal end 26 is connected to a distal end of the pusher wire 20. In some embodiments (not shown), the proximal end 26 and the distal end 28 are connected to the pusher wire 20. Other configurations of attaching the cage 10 to the pusher wire 20 are within the scope of the claims. In some embodiments, the device lacks any mechanism for detaching the cage 10 from the pusher wire 20. Thus, in such embodiments, the cage 10 is removed from a vessel when the pusher wire 20 is pulled out of the vessel.

In some embodiments, such as the one shown in FIG. 2A, cage 10 has a plurality of circumferential bands of cells 30 that form the wall 32 of the cage 10. Each cell 30 is formed by a cell wall 34 having a proximal portion, a central portion, and a distal portion. Each cell wall 34 is formed by a plurality of struts 36. In at least the embodiment shown, the cell wall 34 has a proximal strut pair 38 and a distal strut pair 40. The cell wall 34 defines an opening 42 in the wall 32 of the cage.

In some embodiments configured for shearing, at least one shearing cell has an opening 42 defined by a cell wall having proximally weaker and distally stronger portions such that the cell wall deforms radially inward near a central portion of the cell wall in response to a radially applied force to a greater extent than the distal portion of the cell wall. The radially applied force can, in some instances, occur when the cage contacts the embolus. The radially applied force can also be a uniformly applied force, such as an expansive force. Other radial forces applied to the cage can cause the central portion of the cell wall to deform radially inward to a greater extent than the distal portion of the cell wall. In some embodiments, the deformation of the central portion radially inward is at least about 25% more than the deformation of the distal portion. In some embodiments, the deformation of the central portion radially inward is at least about 30% more than the deformation of the distal portion.

Because cage 10 deforms in this manner, an opening 42 of a shearing cell is able to present itself more favorably to engage with the embolus 12 while the remainder of the cage 10 contacts a greater portion of the wall of the vessel 14. This increased contact area (as well as the stronger distal end in at least some of the openings 42) results in improved shearing of the embolus 12 to sever the fibrin network and trap the embolus 12 into the cage 10 as it is withdrawn proximally.

In at least one of the cells, the central portion of the cell deforms radially inward in response to a radially applied force to a greater extent than the distal portion. Because of this deformation in the cell wall 34 of the at least one shearing cell, in some embodiments the cage 10 has a non-uniform diameter along at least a portion of its length between a proximal end and distal end. In at least one embodiment, an axial length L of the central portion of the shearing cell is at least about 0.5 D, where D is the diameter of the vessel 14 to be treated. In some embodiments, L is at least about 0.75 D. In some embodiments L is about 1.0 D. In some embodiments, L is between about 0.5 D and about 3.0 D.

Figure 3:
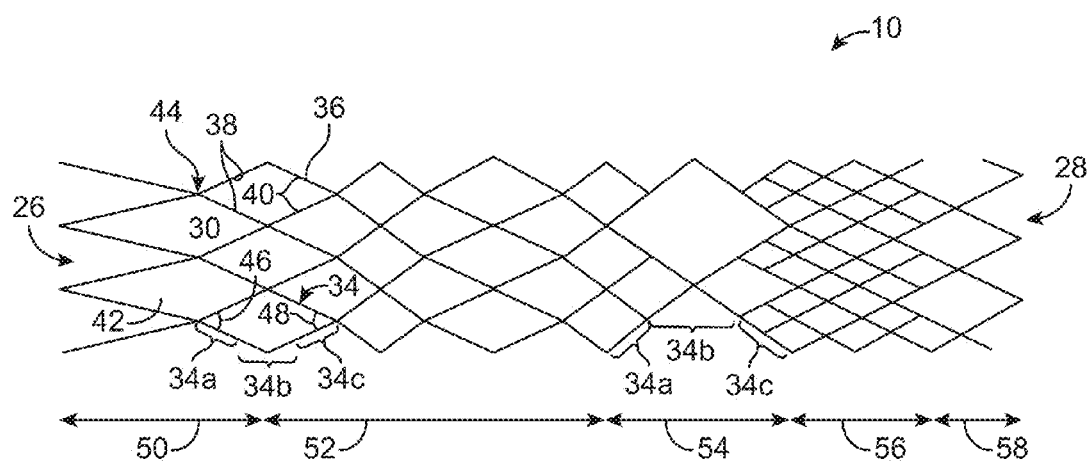
FIG. 3 is a flat view of an embolectomy cage, according to yet another embodiment of the invention.

FIG. 3 shows a flat view of a cage 10 having a plurality of circumferential bands 44 of cells 30. Each cell is a quadrilateral formed by a cell wall 34 having a proximal portion 34a, a central portion 34b, and a distal portion 34c. Each cell wall 34 is formed by a plurality of struts 36. In at least the embodiment shown, the cell wall 34 has a proximal strut pair 38 and a distal strut pair 40. The proximal strut pair 38 has a proximal apex angle 46, and the distal strut pair has a distal apex angle 48.

These cells 30 are arranged into a proximal end region 50 at the proximal end 26 of the cage, a first intermediate region 52, a second intermediate region 54, a third intermediate region 56, and a distal end region 58 at the distal end of the cage. The proximal end region 50 is connected to the first intermediate region 52, which is connected to the second intermediate region 54, which is connected to the third intermediate region 56, which is connected to the distal end region 58. Each region 50, 52, 54, 56, 58 has at least one circumferential band 44 of cells 30.

In the embodiment shown in FIG. 3, each one of these regions 50, 52, 54, 56, 58 has cells 30 with different structures relative to an adjacent region, which creates a non-uniform pattern of cells 30 (and therefore a plurality of non-uniform openings 42) along the length of the cage 10. In some embodiments, this non-uniform pattern of cells 30 (therefore defining a non-uniform pattern of openings 42) allows the cage 10 to have cells 30 of differing radial strengths throughout the cage 10 such that at least one opening is able to engage with a embolus 12 (see FIGS. 1A-E) in a vessel depending on the size or shape of the embolus 12. In some embodiments, the cells 30 are non-uniform in cross-section (by having struts 36 with different widths and/or thicknesses, for example) or non-uniform in size or shape (by having struts 36 with different lengths, for example).

Figure 4:
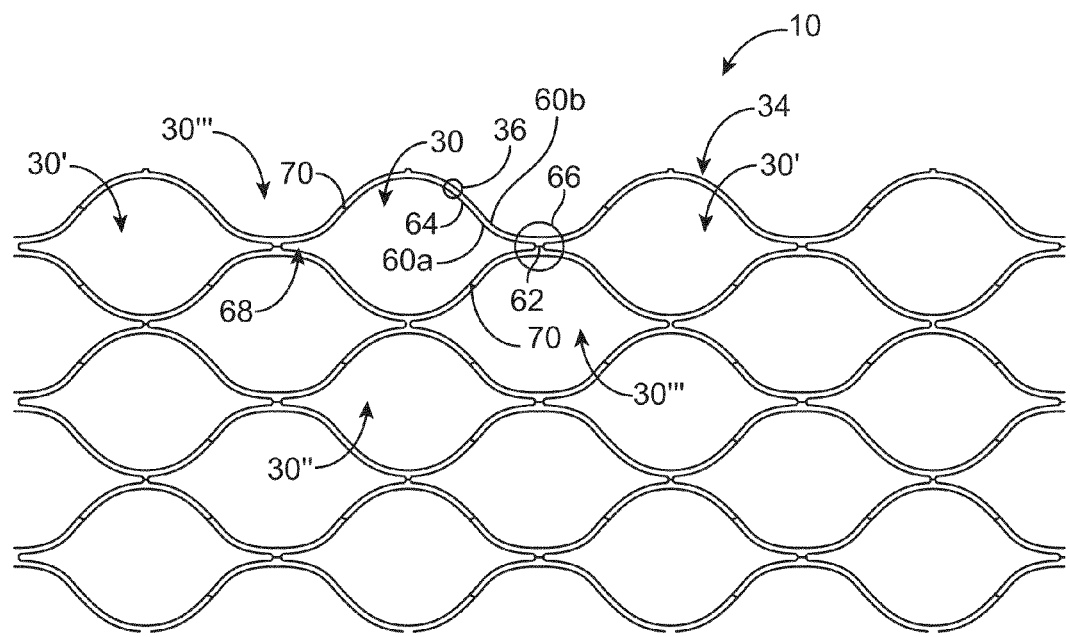
FIGS. 4-6 are detailed flat views of embolectomy cages, according to various embodiments of the invention.

FIG. 4 shows a detailed flat view of a cage 10 according to another embodiment. Each cell 30 has an ovoid shape, more specifically, a "lemon-drop" shape. Of course other cell shapes, such as quadrilateral and hexagonal, are within the scope of the claims.

In the embodiment in FIG. 4, the struts 36 forming the cell wall 34 are each made of a pair of closely spaced, substantially parallel, elongate members 60, an interior elongate member 60a and an exterior elongate member 60b, relative to each cell 30. The interior elongate members 60a of two axially adjacent cells 30, 30' connect to each other, forming a nodal interconnect 62, at a node 66 between cells 30. The nodal interconnects 62 axially connect the cells 30 forming the cell wall 34. Cell 30 also has two circumferentially adjacent cells 30'' (only one shown).

The interior elongate members 60a of each cell 30 connect to the exterior elongate members 60b of that cell 30, forming two inter-nodal interconnects 70, at about "four o'clock" and "ten o'clock" in relation to the cell 30. Because the interior and exterior elongate members 60a, 60b of a cell 30 are the exterior and interior elongate members of an obliquely (i.e., both axially and circumferentially) adjacent cell 30''', the inter-nodal interconnects 70 obliquely connect the cells 30 forming the cell wall 34.

The paired elongate members 60a, 60b define a slot 64, which spans the node 66 between cells 30. Struts 36 with slots 64 that span nodes 66 results in a more flexible cage 10. Because of its increased uninterrupted length adjacent node 66, the exterior elongate members 60b may be more flexible then the interior elongate member 60a at the node 66. The flexibility differential between the two elongate members 60a, 60b may result in the two elongate members 60a, 60b separating from each other in use, when they are under radial pressure from an embolus 12 (see FIGS. 1A-F). This separation of the elongate members 60a, 60b may improve penetration into the embolus 12, due to the smaller size of the elongate members 60a, 60b, and securement to the embolus 12, due to the increased area of contact between elongate members 60a, 60b and the embolus 12. While the elongate members 60a, 60b may separate during use, they may act as a solid strut in response to axially directed forces at the "Y" shapes 68 at the nodes 66 to increase shearing.

In FIG. 4, four internal elongate members 60a, two from each of two axially adjacent cells 30, 30', connect at the node 66 between the cells 30, 30' forming a nodal interconnect 62. Further, two external elongate members 60b pass through the node 66 from one cell 30 to an axially adjacent cell 30'. In this embodiment, there are four connecting elongate members 60, forming one (four elongate member) nodal interconnect 62, and two bypassing elongate members 60 at each node 66, which do not form any connections at the node 66.

The paired elongate member strut construction distributes any force, e.g. radial force, over a greater area while maximizing flexibility. The paired elongate member strut construction also results in no shared elongate members 60 between cells 30. While FIG. 4 shows one particular elongate member splitting and connecting pattern, other patterns are also within the scope of the claims.

Figure 5:
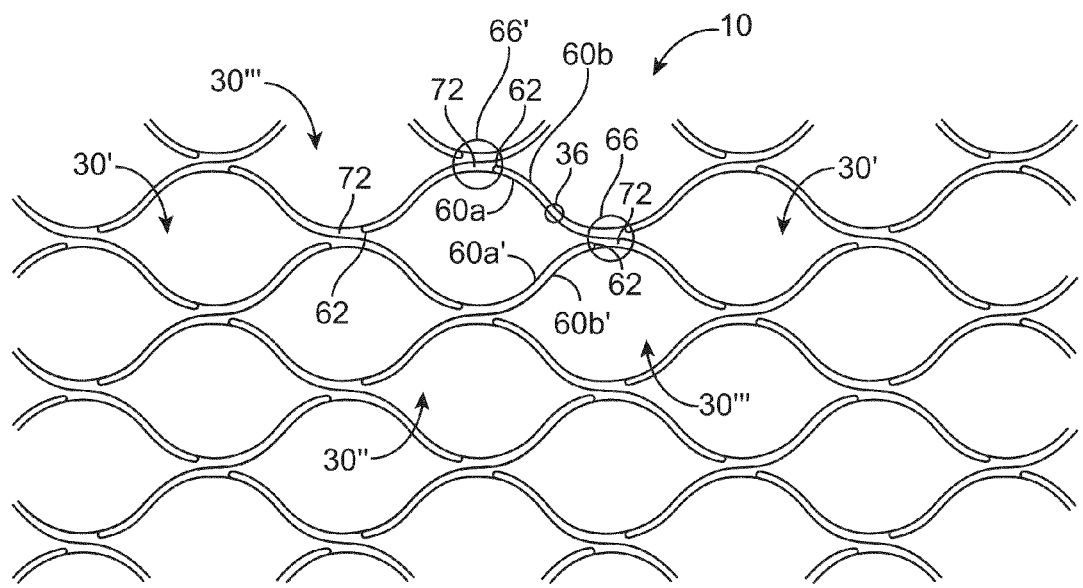

For instance, FIG. 5 illustrates a detailed flat view of a cage 10 according to another embodiment. All connections between cells 30 in this embodiment occur at nodes 66, 66'. Obliquely adjacent cells 30, 30''' are connected at circumferential nodes 66' (relative to cell 30) positioned at "twelve o'clock" and "six o'clock." Axially adjacent cells 30, 30' are connected at axial nodes 66. Whether a node is an axial node 66 or a circumferential node 66' depends on the cell that anchors the frame of reference.

While the struts 36 forming the cell wall 34 of this cage 10 are also each made of a pair of substantially parallel elongate members 60, the elongate members 60 are not continuous. Each external elongate member 60b contains a break 72 between axial nodes 66, and each internal elongate member 60a contains a break 72 at each axial node 66.

Four elongate members 60 from each cell 30 are disposed at each axial node 66. One internal elongate member 60a terminates by connecting to its parallel external elongate member 60b at the axial node 66. The other internal elongate member 60a' passes through the axial node 66 from one cell 30 to an axially adjacent cell 30'. Once the internal elongate member 60a' passes through the axial node 66, it becomes the internal elongate member 60a' on the opposite side of the axially adjacent cell 30'. In this embodiment, there are six connecting elongate members 60, forming two (three elongate member) nodal interconnects 62, and one bypassing elongate member 60a' at each axial node 66, which does not form any connections at the axial node 66. In this embodiment, three elongate members (60a', 60b, 60b') from each cell 30 interconnect at the axial node 66 and one elongate member (60a') bypasses the axial node 66.

Four elongate members 60 from each cell 30 are disposed at each circumferential node 66'. One external elongate member 60b' terminates by connecting to its parallel internal elongate member 60a at the circumferential node 66'. The other external elongate member 60b passes through the circumferential node 66' from one cell 30 to an obliquely adjacent cell 30'. Once the external elongate member 60b passes through the circumferential node 66', it becomes the external elongate member 60a on the opposite side of the obliquely adjacent cell 30'. In this embodiment, there are six connecting elongate members 60, forming two (three elongate member) nodal interconnects 62, and one bypassing elongate member 60b at each circumferential node 66', which does not form any connections at the circumferential node 66'. In this embodiment, three elongate members (60a, 60a', 60b') interconnect at the circumferential node 66' and one elongate member (60b) bypasses the circumferential node 66'.

Figure 6:
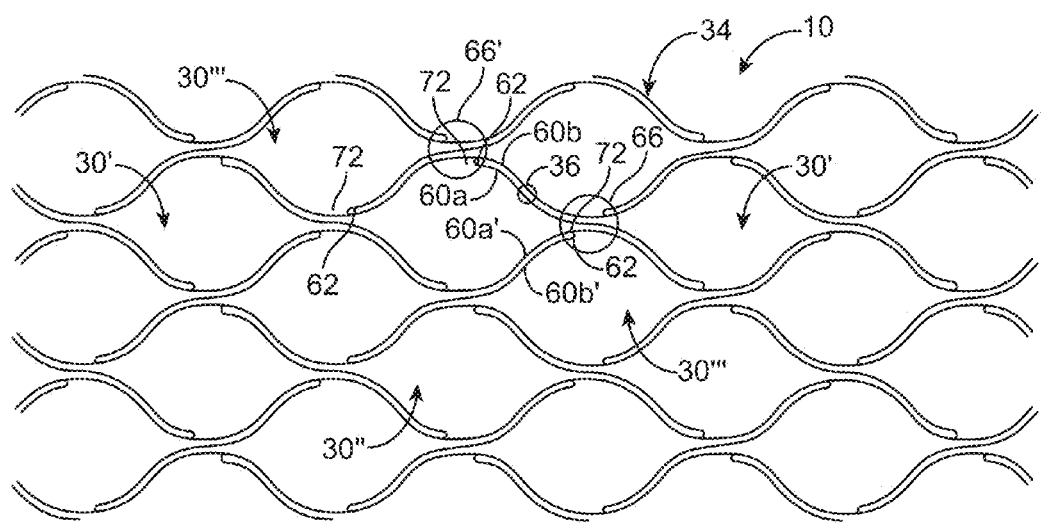

The embodiment in FIG. 6 is similar to the one in FIG. 5. Like the embodiment in FIG. 5, all connections between cells 30 in the embodiment in FIG. 6 occur at nodes 66, 66'. Obliquely adjacent cells 30, 30''' are connected at circumferential nodes 66' (relative to cell 30) positioned at "twelve o'clock" and "six o'clock." Axially adjacent cells 30, 30' are connected at axial nodes 66.

While the struts 36 forming the cell wall 34 of this cage 10 are also each made of a pair of substantially parallel elongate members 60, the elongate members 60 are not continuous. Each internal elongate member 60a contains a break 72 between axial nodes 66, and each external elongate member 60b contains a break 72 at each axial node 66. At the break 72 in the internal elongate member 60a between axial nodes 66, an internal elongate member 60a connects with the parallel external elongate member 60b at a nodal interconnect 62 at a circumferential node 66'. At that point, the parallel external elongate member 60b becomes the internal elongate member 60a, which is separated from its parallel external elongate member 60b by the break 72.

Four elongate members 60 from each cell 30 are disposed at each axial node 66. One external elongate member 60b terminates by connecting to its parallel internal elongate member 60a at the axial node 66. The other internal elongate member 60a' passes through the axial node 66 from one cell 30 to an axially adjacent cell 30'. Once the internal elongate member 60a' passes through the axial node 66, it becomes the internal elongate member 60a on the opposite side of the axially adjacent cell 30'. In this embodiment, there are six connecting elongate members 60, forming two (three elongate member) nodal interconnects 62, and one bypassing elongate member 60a' at each axial node 66, which does not form any connections at the axial node 66. In this embodiment, three elongate members (60a, 60b, 60b') interconnect at the axial node 66 and one elongate member (60a') bypasses the axial node 66.

Four elongate members 60 from each cell 30 are disposed at each circumferential node 66'. One internal elongate member 60a terminates by connecting to its parallel external elongate member 60*b* at the circumferential node 66'. The other external elongate member 60*b* passes through the circumferential node 66' from one cell 30 to an obliquely adjacent cell 30'''. Once the external elongate member 60*b* passes through the circumferential node 66', it becomes the internal elongate member 60*a* on the opposite side of the obliquely adjacent cell 30'''. In this embodiment, there are six connecting elongate members 60, forming two (three elongate member) nodal interconnects 62, and one bypassing elongate member 60*b* at each circumferential node 66', which does not form any connections at the circumferential node 66'. In this embodiment, three elongate members (60*a*, 60*a*', 60*b*') from each cell 30 interconnect at the circumferential node 66' and one elongate member (60*b*) bypasses the circumferential node 66'.

Figure 10:
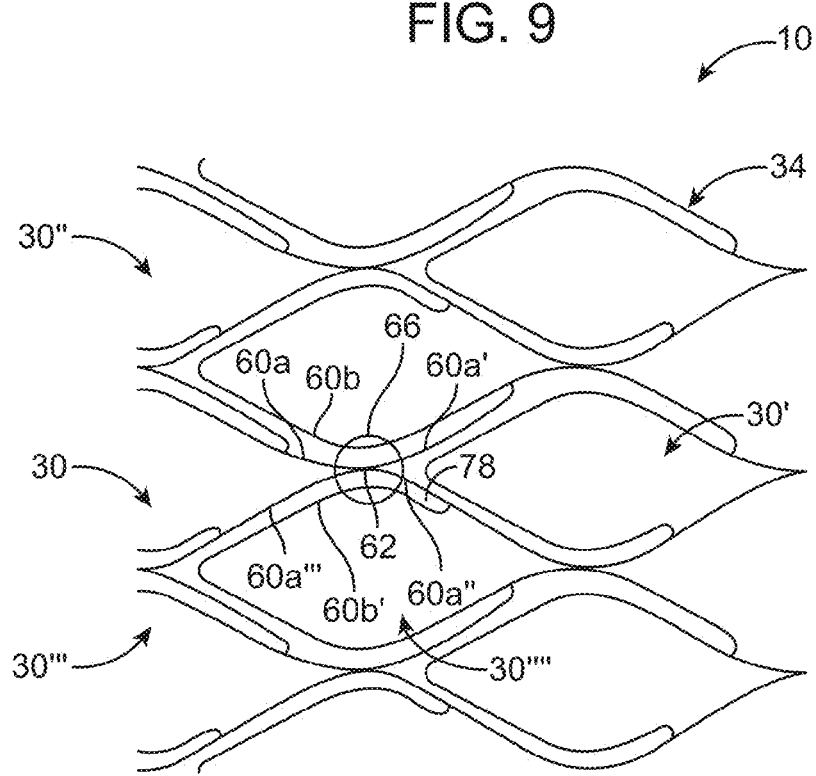
FIG. 10 is a detailed flat view of an embolectomy cage, according to yet another embodiment of the invention.

FIG. 10 illustrates a detailed flat view of a cage 10 according to yet another embodiment. The axial nodes 66 in this embodiment are similar to those in the embodiment in FIG. 4 in that four elongate members 60*a*, 60*a*', 60*a*'', 60*a*''' of two axially adjacent cells 30, 30' connect to each other at the node 66, forming a nodal interconnect 62. The nodal interconnects 62 axially connect the cells 30 forming the cell wall 34. Cell 30 also has two circumferentially adjacent cells 30". In this embodiment, at each node 62, there is an elongate member 60*b*' that spans the node without forming a connection and remains within a single cell 30"", forming an un-connected leaf 78.

The cells 30 in the embodiments in FIGS. 4-6 and 10 are "closed," in that there are no free ends in the longitudinal direction that could interfere with the unsheathing and re-sheathing of the embolic cage 10. Such free ends could snag on and damage the catheter 18 and vessel 14.

In any of the embodiments, the internal and external elongate members (60*a*, 60*b*) may have different flexibilities to maximize the flexibility differential between the two elongate members 60*a*, 60*b*. For instance, the internal and external elongate members (60*a*, 60*b*) may have different cross-sectional shapes, i.e., circular, ovoid, rectangular, triangular, etc.

Further, the struts 36 may have portions with paired elongate member construction and other portions with solid construction to more precisely control the flexibility of portions of the struts 36, cells 30, and cages 10.

Figure 7A:
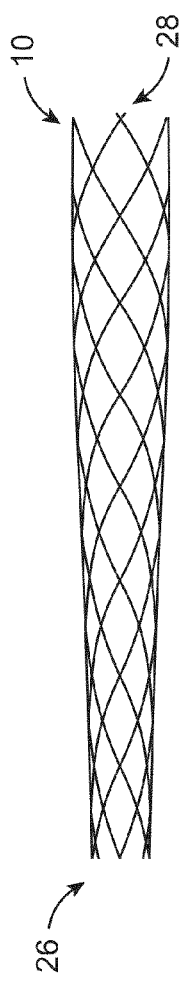
FIG. 7A is a plan view of an embolectomy cage, according to still another embodiment of the invention.
Figure 7B:
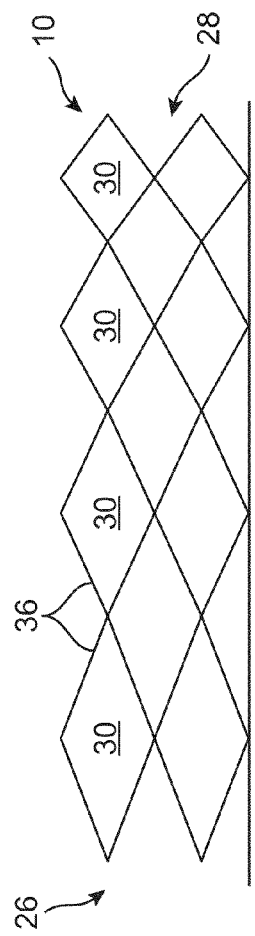
FIGS. 7B-7D are flat views of embolectomy cages, according to various embodiments of the invention.
Figure 7C:
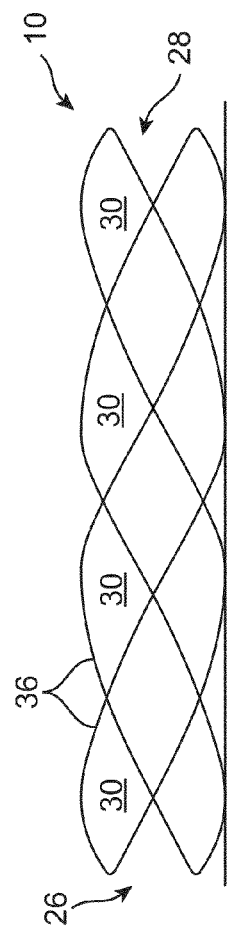
Figure 7D:
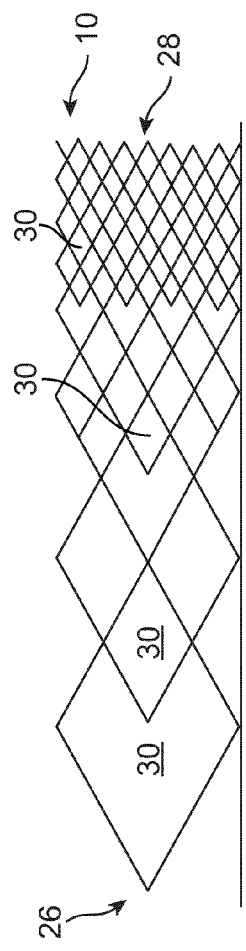

In at least one embodiment, upon full expansion, cage 10 has generally constant diameter along at least a portion of its length. In other embodiments, it may be desirable to have a cage with a tapered diameter from a proximal end 26 to a distal end 28 (or at least a portion thereof) or conversely the cage 10 has a tapered diameter from the distal end 28 to the proximal end 26 (or at least a portion thereof), as shown in FIG. 7A, upon full expansion of the cage. Various methods can be used to create a cage with a tapered diameter. A tapered diameter of the cage can be accomplished by progressively shortening the lengths of the struts 36 of each cell 30 along the length of the cage from the proximal end 26 to the distal end 28 (as shown in FIG. 7B), by progressively increasing the width or thickness of the struts 36 of each cell 30 along the length of the cage from the proximal end 26 to the distal end 28 (as shown in FIG. 7C), by progressively increasing cell density (in other words, the number of cells 30 per area) along the length of the cage from the proximal end 26 to the distal end 28 (as shown in FIG. 7D), or by other suitable methods.

In some embodiments, it may be desirable to have a cage with a variable diameter from the proximal end to a distal end upon full expansion, such that the diameter increases and decreases repetitively along at least a portion of the length of the cage 10, as shown in FIG. 8A. Such a cage 10 can be accomplished by having proximal strut pair 38 with struts 36 of a length that is longer than the length of the struts 36 of the distal strut pair 40 (as shown in FIG. 8B), by having distal strut pair 40 with thicker or wider struts 36 of a length that is longer than the length of the struts 36 of the proximal strut pair 38 (as shown in FIG. 8C), by increasing the number of cells 30 (or increasing the cellular density) in the locations where a smaller diameter is desired (as shown in FIG. 8D), or by other suitable methods. Other configurations of the cage (such as tapered diameters in some portions of the cage and variable diameters elsewhere along the cage and other combinations) are within the scope of the claims.

Figure 9:
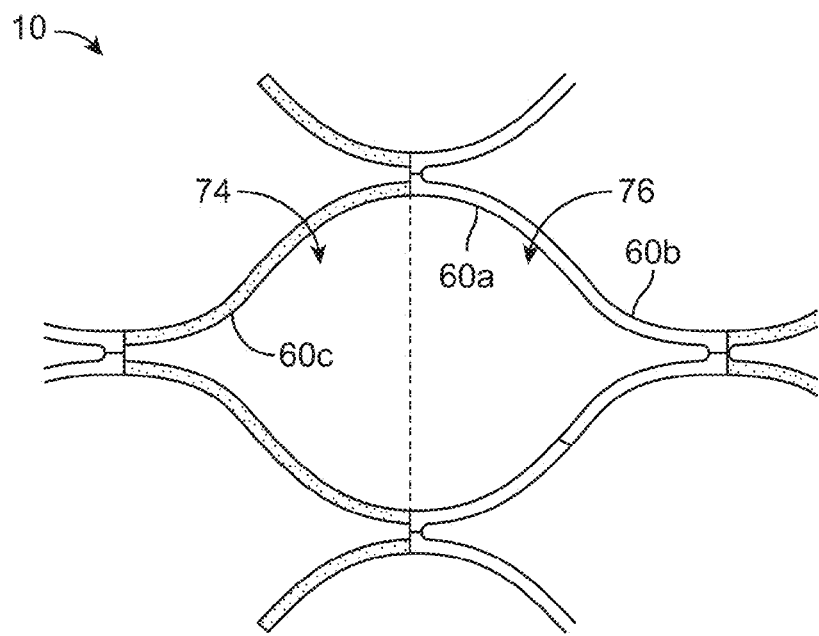
FIG. 9 is a detailed flat view of an embolectomy cage, according to another embodiment of the invention.

The embolectomy cage 10 in FIG. 9 is made of paired elongate members 60*a, b* and unpaired elongate members 60*c*. Each cell 30 defined by the elongate members 60 has two regions 74, 76. One region 74, generally on the left side in FIG. 9 or proximal on the embolectomy cage 10, is defined by unpaired elongate members 60*c*. The other region 76, generally on the right side in FIG. 9 or distal on the embolectomy cage 10, is defined by paired elongate members 60*a, b*. Although the unpaired elongate member 60*c* is different size from the paired elongate members 60*a, b* in this embodiment, the elongate members 60*a*, 60*b*, 60*c* can be the same size.

In some embodiments, the embolectomy cage 10 may be laser cut from a tube. It may also be cut from a flat sheet and welded at a seam.

In some embodiments, the cage may be provided with a distally mounted catchment or net. In such embodiments, the proximal section of the net should be a high radial pressure region to ensure the net opens up to the greatest extent of the vessel lumen as possible.

In some embodiments, the wall of the cage 10 is formed of a structural material that is present everywhere along the wall in a single layer between the proximal end and the distal end. In at least one embodiment, the cage 10 is cut from a solid tube comprised of metals, polymers, composites and other materials, such as nitinol, PET, PTFE, and other biocompatible materials. The cage can also be of a molded or other non-wire construction. In some embodiments, the wall of the cage can be formed by braiding a wire of material such as nitinol, PET, PTFE and other biocompatible materials about a mandrel.

In some embodiments, the cage is fully or partially coated on any surface of the cage with a substance, including but not limited to a drug, genetic material, cells, a therapeutic agent, a polymer matrix having a therapeutic component, a thrombolytic substance used to dissolve the embolus, or any other substance which would desirable to deliver into a body lumen. The therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

What is claimed is:

1. An embolectomy cage having an elongate axis and a circumference, comprising:
    a plurality of paired, closely spaced, substantially parallel, elongate members arranged in a direction of the elongate axis and forming nodal and inter-nodal connections of the embolectomy cage along the elongate axis and about the circumference, wherein the pairs of elongate members collectively define a plurality of open cells,
    wherein an inner elongate member of a first pair of elongate members is connected to an inner elongate member of a second pair of elongate members at a first node located between a first pair of axially adjacent cells and a first pair of circumferentially adjacent cells, and wherein the inner elongate member of the first pair of elongate members is circumferentially spaced from the inner elongate member of the second pair of elongate members,
    wherein an outer elongate member of the first pair of elongate members and an outer elongate member of the second pair of elongate members each spans the first node without connection to another node, and wherein the outer elongate member of the second pair of elongate members forms a second node with an outer elongate member of a third pair of elongate members, the second node located between a second pair of axially adjacent cells and a second pair of circumferentially adjacent cells,
    wherein the inner elongate member of the first pair of elongate members is also connected to the inner elongate member of the second pair of elongate members at a third node that is axially spaced from the first node, wherein the second node is located between the first and third node along the elongate axis,
    wherein the inner and outer elongate members of the first pair of elongate members are connected to each other at a first inter-nodal interconnect located between the first node and the third node, and
    wherein the inner and outer elongate members of the second pair of elongate members are connected to each other at a second inter-nodal interconnect located between the first node and the second node.

2. The embolectomy cage of claim 1, wherein one of the inner elongate member and the outer elongate member of the first pair of elongate members is more flexible than the other.

3. The embolectomy cage of claim 1, wherein the inner elongate member of the first pair of elongate members has a different cross-sectional geometry than the outer elongate member of the first pair of elongate members.

4. The embolectomy cage of claim 1, at least one cell of the first pair of axially adjacent cells comprising a proximal region bordered by proximally located portions of the first and second pairs of elongate members, and a distal region bordered by distally located portions of the first and second pairs of elongate members.

5. The embolectomy cage of claim 4, wherein the proximally located portions of the first and second pairs of elongate members have substantially same respective lengths as the distally located portions of the first and second pairs of elongate members.

6. The embolectomy cage of claim 4, wherein the proximally located portions of the first and second pairs of elongate members have respective lengths that are greater than the respective lengths of the distally located portions of the first and second pairs of elongate members.

7. The embolectomy cage of claim 4, wherein the distally located portions of the first and second pairs of elongate members have greater lengths than the proximally located portions of the first and second pairs of elongate members.

8. The embolectomy cage of claim 1, wherein the respective first elongate members of the first and second pair of elongate members form boundaries of each cell of the first pair of axially adjacent cells.

9. The embolectomy cage of claim 1, wherein at least one cell-of the first pair of axially adjacent cells is ovoid in shape.

10. The embolectomy cage of claim 1, wherein at least one cell of the first pair of axially adjacent cells is hexagonal in shape.

11. The embolectomy cage of claim 1, wherein the cells of the first pair of axially adjacent cells are substantially uniform in shape.

12. The embolectomy cage of claim 1, wherein an inner elongate member of the third pair of elongate members spans the second node without connection to another elongate member.

* * * * *